United States Patent [19]

Schinzel et al.

[11] 3,972,877

[45] Aug. 3, 1976

[54] BUTADIENE DERIVATIVES, PROCESS FOR THEIR PREPARATION AND THEIR USE AS OPTICAL BRIGHTENERS

[75] Inventors: Erich Schinzel, Hofheim, Taunus; Wilfried Sahm, Kelkheim, Taunus; Günter Rösch, Altenhain, Taunus, all of Germany

[73] Assignee: Hoechst Aktiengesellschaft, Frankfurt am Main, Germany

[22] Filed: Jan. 7, 1974

[21] Appl. No.: 431,047

[30] Foreign Application Priority Data

Jan. 12, 1973   Germany.............................. 2301410

[52] U.S. Cl....................... 260/240 R; 252/301.22
[51] Int. Cl.²...................................... C07D 307/79
[58] Field of Search..................... 260/240 R, 240 D

[56] References Cited
UNITED STATES PATENTS

| 2,166,736 | 7/1939 | White et al.................... 260/240.8 |
| 2,255,077 | 9/1941 | Middleton....................... 260/240 D |
| 3,382,240 | 5/1968 | Iwai et al. ...................... 260/240 D |
| 3,384,487 | 5/1968 | Heseltine et al................ 260/240.1 |
| 3,821,205 | 6/1974 | Fumia et al..................... 260/240 D |
| 3,833,863 | 9/1974 | Webster et al.................. 260/240.9 |

FOREIGN PATENTS OR APPLICATIONS

| 4,531,298 | 1970 | Japan |
| 1,189,330 | 11/1967 | United Kingdom |

OTHER PUBLICATIONS

Shimizu, Chem. Abstracts, 1963, Col. 533–544.
Kobayashi, Chem. Abstracts. 76(1972).
Tarnopolskii et al., Chem. Abstracts, 77(1972).
Compton et al., J. Org. Chem. 1947, pp. 363–367.
Saikachi et al., Chemical Abstracts, 70(1969).

*Primary Examiner*—Arthur P. Demers
*Attorney, Agent, or Firm*—Connolly and Hutz

[57] ABSTRACT

1,3-butadienes containing at least one terminal 2-benzofuranyl group are obtainable by HORNER syntheses. The products are optical brighteners.

7 Claims, No Drawings

BUTADIENE DERIVATIVES, PROCESS FOR THEIR PREPARATION AND THEIR USE AS OPTICAL BRIGHTENERS

The present invention relates to butadiene derivatives, to a process for their preparation and their use as optical brighteners.

German Patent Specification No. 1,138,757 discloses the preparation of 1,1,4,4-tetraphenyl-butadiene-(1,3), starting from ethylene-1,2-bis-diphenyl-phosphinoxide and benzophenone, and the use of these and similar compounds as scintillators and as optical brighteners.

The invention comprises a compound of the formula

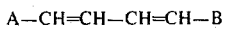
A—CH=CH—CH=CH—B in which A is phenyl, naphthyl, 2-thienyl, 2-furanyl or 2-benzofuranyl which radicals are unsubstituted or substituted by lower alkyl, lower alkoxy, phenyl, carboxy, sulfo, cyano or lower carboalkoxy; and B is 2-benzofuranyl or lower alkyl-2-benzofuranyl.

Also encompassed by the invention is a compound of the formula

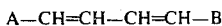
A—CH=CH—CH=CH—B wherein A is phenyl, naphthyl, 2-thienyl, 2-furanyl, 2-benzofuranyl or phenyl substituted by lower alkyl, lower alkoxy, phenyl, carboxy, sulfo, cyano or lower carboalkoxy; and B is 2-benzofuranyl or lower alkyl-2-benzofuranyl.

The invention relates to new butadiene derivatives which are colorless or slightly yellow and which have, in a dissolved state, a more or less marked violet-blue to greenish blue fluorescence and correspond to the formula

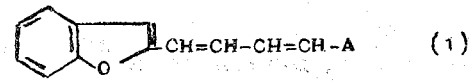

in which A is a phenyl, naphthyl, 2-thienyl, 2-furanyl or 2-benzofuranyl group, which aromatic radicals may be substituted by non chromophoric radicals.

As non-chromophoric substituents there are considered above all: (preferably lower) alkyl, (preferably lower) alkenyl, (preferably lower) alkoxy groups, aryl radicals, preferably phenyl radicals, aralkyl groups which preferably derive from lower alkylene and phenyl radicals, such as benzyl and phenylethyl groups, acyl groups, optionally functionally modified carboxy or sulfo groups, acylamine or sulfonyl groups as well as halogen atoms.

Functionally modified carboxy groups are generally carboxylic acid derivatives in the widest sense, i.e. compounds with one carbon atom, from which three bonds are linked to hetero atoms, especially oxygen, nitrogen and sulfur. In a narrower sense they are salts with colorless cations, alkali metal or ammonium ions being preferred, and furthermore the cyano group, the carboxylic acid ester group or the carboxylic acid amide group. Carboxylic acid ester groups are especially those of the general formula $COOR^5$, in which $R^5$ is phenyl or an optionally branched lower alkyl group, which radicals may contain further substituents, such as a preferably low-molecular dialkylamino, lower trialkyl ammonium, a hydroxy or a lower alkoxy group.

A carboxylic acid amide group is especially one of the formula $CONR^6R^7$, in which the radicals $R^6$ and $R^7$ represent hydrogen atoms or lower, optionally hydroxy- substituted, alkyl groups, which, jointly with the nitrogen atoms, may form a hydro-aromatic ring, furthermore acid hydrazides and the analogous thio derivatives.

Functionally modified sulfo groups are — by analogy to the preceding explanations — radicals, the sulfone group of which is bound to a hetero atoms, i.e. the sulfonic acid salts with colorless cations, preferably alkali metal or ammonium ions, and furthermore the sulfonic acid ester group and the sulfonamide group. A sulfonic acid ester group is especially one of the formula $SO_2OR^5$, in which $R^5$ has the above meaning, and a sulfonamide group is one of the formula $SO_2NR^6R^7$, in which $R^6$ and $R^7$ have the above meanings.

An acyl group is especially one of the formula $COR^8$, in which $R^8$ stands for an optionally substituted, preferably lower alkyl or phenyl radical, especially an unsubstituted lower alkanoyl group or the benzoyl group.

A sulfonyl radical is especially one of the formula $SO_2R^9$, in which $R^9$ stands for an optionally substituted lower alkyl or phenyl group, which groups may preferably contain as substitutents a lower dialkylamino, lower trialkyl ammonium, acylamino or sulfo group.

The compounds according to the invention may be prepared in different ways. The methods of preparation preferred are detailed in the following:

According to HORNER

I. a phosphorus compound of the formula (2)

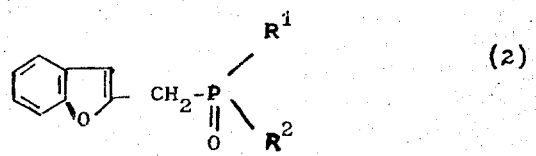

is condensed with an acrolein derivative of the formula (3)

OCH—CH=CH—A  (3)

or

II. a phosphorus compound of the formula (4)

is condensed with an acrolein derivative of the formula (5)

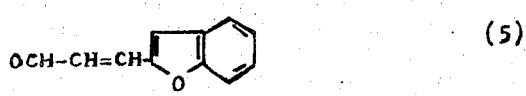

It is also possible to react

III. a phosphorus compound of the formula (6)

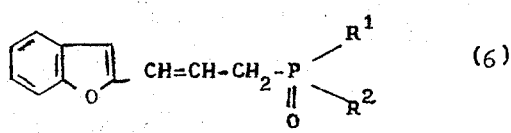

with an aldehyde of the formula (7)

OCH—A (7)

or

IV. a phosphorus compound of the formula (8)

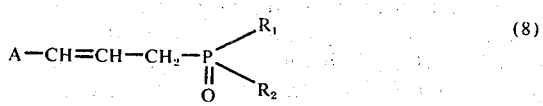

(8)

with an aldehyde of the formula (9)

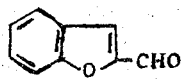

(9)

The intermediate products (3), (5), (6) and (8) may themselves be prepared by HORNER reactions. Both double bonds of the butadiene chain may also be snythetized in HORNER reactions with a bifunctional component, for example according to the process of German Patent Specification No. 1,138,757. In the formulae (3), (4), (7) and (8) A has the meaning indicated in the general formula (1). In the formulae (2), (4), (6) and (8) $R^1$ and $R^2$ stand, respectively, for identical or different alkyl, cycloalkyl, aralkyl or aryl radicals optionally bound via an oxygen atom. Since the radicals $R^1$ and $R^2$ do not appear in the final product, their chemical nature is irrelevant with regard to the product of the process. For practical reasons, however, cyclohexyl, benzyl, phenyl and especially lower alkyl radicals are preferred.

The processes mentioned are preferably carried out in inert solvents, such as hydrocarbons, for example toluene or xylene, or alcohols, such as methanol, ethanol, isopropanol, butanol, glycol, hexanol, cyclohexanol, cyclooctanol, furthermore in ethers, for example diisopropyl ether, glycol ethers, as for example 2-methoxy-ethanol, dioxane, tetrahydro-furan, furthermore in formamides and N-methyl-pyrrolidone. Especially sitable are dipolar organic solvents such as dimethylformamide and dimethyl sulfoxide.

As condensation agents strongly alkaline compounds, for example alkali metal or alkaline earth metal hydroxides, alkali metal or alkaline earth metal amides are used, preferably potassium hydroxide, sodium hydroxide, potassium-tert.-butylate or sodium methylate, furthermore the alkali metal compounds of dimethyl sulfoxide and alkali metal hydrides.

Depending on the nature of the starting materials the reaction temperature is between about 0° and about 100°C, preferably between about 10° and about 80°C.

The compounds of the invention are also obtained when using instead of the phosphorus compounds (2), (4), (6) and (8) the corresponding quarternary phosphonium salts, for example the triphenyl-phosphonium salts and condensing these compounds according to WITTIG via the phosphorylenes with the aldehydes (3), (5), (7) and (9).

Already known processes for preparing 1,4-diarylbutadienes are based on the condensation of arylacetic acids with cinnamaldehydes in the presence of acetanhydride or of β-benzenepropionic acids with benzaldehydes, whereby preferably lead oxide is used as a catalyst (Organ. Synth. Coll. Vol. II, 229). Naturally the reaction products of the above processes may be subjected to other known modifications, for example to sulfonations with sulfonating agents, as for example $H_2SO_4$, mixtures of $H_2SO_4$ and $SO_3$, amidosulfonic or chlorosulfonic acid, furthermore the modifications which — starting for example from molecules containing sulfo or carboxy groups, lead to compounds having functionally modified sulfo or carboxy groups, or the conversions of such groups into other groups of this type or into the free acids.

Especially by using the compounds described by the general formulae (2) to (9) with the radical A defined therein and, if desired, by a further conversion of the condensation products so obtained, the following compounds may be prepared for example:

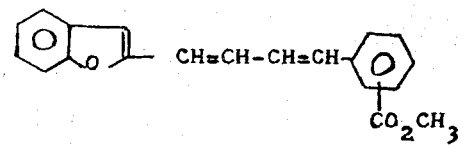

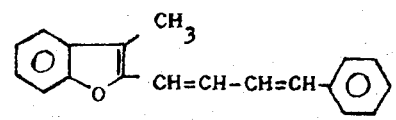

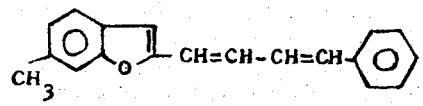

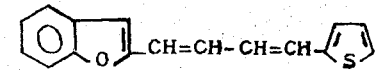

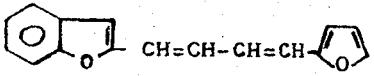

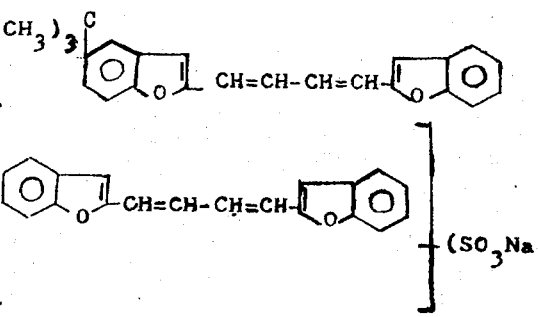

Due to their fluorescence power the novel compounds according to the invention have a large field of application. They serve above all as optical brighteners for very different natural and synthetic organic materials, which also include organic materials which may be used for finishing mineralic materials, for example inorganic pigments.

The substrates to be brightened are, for example, of the following materials: lacquers, synthetic fibres for example, consisting of acetyl cellulose, polyesters, polyamides, polyolefines, polyvinyl chloride, polyvinylidene chloride or polyacrylonitrile as well as foils, films, ribbons or shaped articles made of such materials.

The water-insoluble compounds according to the invention may be used in dissolved form in organic solvents or in an aqueous dispersion, preferably by means of a dispersing agent.

There may be mentioned as dispersing agents, for example, soaps, polyglycol ethers deriving from fatty alcohols, fatty amines or alkyl phenols, cellulose sulfite waste liquors or condensation products of optionally alkylated naphthalene sulfonic acids with formaldehyde.

The water-soluble anionic compounds according to the invention are especially suitable for the optical brightening of native and regenerated cellulose fibres and of wool and synthetic polyamide fibres.

The cationic compounds according to the invention which are soluble in water or diluted acid are especially suitable for the optical brightening of mixed polymers of acrylonitrile, especially the commercial copolymers having a contents of at least 85 % of acrylonitrile.

The butadiene derivatives of the general formula (1) may also be added to laundry detergents. These detergents may contain the usual fillers and auxiliaries, for example, alkali metal silicates, alkali metal phosphates or condensed phosphates, alkali metal borates, alkali metal salts of carboxymethyl cellulose, foam stabilizers, as, for example, alkanol amides of higher fatty acids or complex formers, for example, soluble salts of the ethylene diamine tetraacetic acid or diethylene-triaminepentaacetic acid as well as chemical bleaching agents, as for example perborates or percarbonates, perborate activators of the polyacetic acid amide type, which faciliate the formation of peracetic acid from peroxo-compounds and, further, disinfectants.

The fibre material is brightened with the aqueous or, if desired, organic brightening liquor either by the exhaustion process at temperatures preferably within the range of from 20° to 150°C or under thermosol conditons; by this process the textile material is impregnated or sprayed with the brightening solution or dispersion and squeezed between rollers to a content of residual moisture of about 50 to about 120 %, referred to dry weight. The textile material is then subjected to a heat treatment for about 10 to about 300 seconds, preferably to dry heat at about 120° to about 240°C. This thermosol process may be combined with other finishing operations, for example together with synthetic resins for an "easy care" finish; wherein, if desired, after impregnation and drying at 100°-150°C the material is condensed for 5 to 20 minutes at 150°-200°C for cross-linking.

Furthermore, the compounds according to the invention may be added to high-molecular organic materials before or during their shaping. Thus, they may be added to the molding materials in the preparation of fibres, films, foils, ribbons or shaped articles or dissolved in the spinning mass before the spinning process. Suitable compounds may also be added to the low-molecular-weight starting materials before polycondensation or polymerization, as in the case of polyamide-6, polyamide-6,6 or linear esters of the polyethylene glycol terephthalate type.

Compounds according to the invention substituted by one or preferably two carboxy or carbo-alkoxy groups, may be bound to linear polyester molecules and synthetic polyamides by an ester or amide bond, if they are added to these materials or preferably to their starting compounds under suitable conditions. The brighteners linked by this way to the substrate by a chemical bond, show an extremely high fastness to sublimation and to solvents.

Olefinically unsaturated compounds according to the invention which contain besides the fluorescent system at least one olefinic double bond capable of being polymerized, may be used for preparing fluorescent polymers or polymer mixtures, by polymerizing them as such or in mixture with other monomer or polymer vinyl compounds, whereby the fluorescent system is maintained. These fluorescent polymers may be subsequently mixed with not fluorescent polymers. Polymers optically brightened in this manner show a high degree of whiteness. Furthermore, the chemical bond of the brightener molecules to the polymers ensures a high fastness to sublimation and to solvents.

The amount of the compounds to be used according to the invention having the general formula (1), calculated on the material to be optionally brightened, may vary within wide limits, according to the field of application and to the effect desired. It may be easily determined by tests and generally ranges between about 0.01 and about 2 %.

The following Examples illustrate the invention. Parts and percentages are by weight, unless otherwise stated. The ratio of parts by weight and by volume are that of the kilogram to the liter.

EXAMPLE 1

1-phenyl-4-[cumaronyl-(2')]-butadiene-(1,3)

(101):

127.6 g of 2-bromomethyl-cumarone (prepared from 2-methylcumarone with the aid of N-bromo-succinimide) having a solidification point of 36.6°C, 200 ml of triethyl phosphite and 300 ml of dimethylformamide were heated, while stirring, to 120°C and heated in the course of 4 hours up to 150°C. Then the dimethylformamide and triethyl phosphite were distilled off from the mixture and the remaining oily residue was distilled under reduced pressure (0.3 mm mercury) up to a distillation temperature of 50°C at the heat of the column. The oily cumaronyl-(2)-methyl-phosphonic acid diethyl ester (140 g) thus obtained was found to be 90 % upon gas chromatographic analysis.

When condensing this phosphonic acid ester with cinnamaldehyde in dimethylformamide and using a suspension of ground sodium or potassium hydroxide as condensation agent the compound (101) was obtained in a crude state with a yield of 96 % of the theory. Redissolved in n-butanol/charcoal the compound (101) formed yellow crystals having a constant melting point of 152° to 154°C. The cumaronyl-butadienes (102) to (107) were prepared in an analogous manner.

As reaction medium may further be preferably used methanol, ethanol and n-butanol.

EXAMPLE 2

1,4-bis-[cumaronyl-(2')]-butadiene-(1,3)

(108):

73 g of benzofuran-2-aldehyde were dissolved in 228 ml of acetaldehyde and cooled to −20°C. At this temperature, a solution of 3.67 g of potassium hydroxide in 18.5 ml of absolute ethanol was dropped to this mixture, while stirring, in about 10 minutes. The whole was stirred for one hour at −20°C and stirring was continued for 2 hours at 0°C. Subsequently, 61.5 ml of acetanhydride were added, and the mixture was distilled under normal pressure, until a transition temperature of 85°C was reached. The distillation residue was mixed with 450 ml of water and 1 ml of concentrated hydrochloric acid and stirred for 3 hours under reflux. It was allowed to cool, the residue suction-filtered and washed neutral with water. After drying under reduced pressure at 40°C, 62.2 g (72.2 % of the theory) of crude 2-(cumaronyl-2')-acrolein were obtained. Recrystallized from cyclohexane, this aldehyde melted at 65°–67°C.

10.5 g of the cumaronyl-(2)-methyl-phosphonic acid diethyl ester (according to Example 1) and 5.2 g of 2-[cumaronyl-(2')]-acrolein were dissolved in 30 ml of dimethylformamide and added dropwise, in about 15 minutes, to a suspension heated to 30°–40°C of 5 g of potassium-tert.-butylate in 70 ml of dmethylformamide. Stirring was continued for 45 minutes at room temperature, then the batch was poured onto 900 ml of ice water and neutralized with concentrated hydrochloric acid. After stirring was continued for a short time the mixture was suction-filtered and washed free from ions with water. After drying under reduced pressure 8.11 g of the compound (108) (94.4 %) were obtained in the form of a brownish powder. By purification from chlorobenzene under addition of bleaching earth, yellow crystals having a melting point of 232° to 235°C were obtained.

EXAMPLE 3

In a glass apparatus provided with a stirrer, a gas inlet pipe, a vacuum device and a descending cooler, 400 g of dimethyl-terephthalate, 310 g of ethylene glycol and 0.5 g of antimony oxide were heated under nitrogen to an external temperature of about 200°C. This temperature was maintained for 3 hours, while methanol was slowly distilling off. Then 0.5 g of the compound (101) and 20 g of a 20 % TiO$_2$-suspension in ethylene glycol were added, the external temperature was raised to 285°C and while slowly reducing the pressure to 0.2 mm of mercury, the ethylene glycol was distilled off in the course of three hours. The block of optically brightened polyester material obtained by this way was comminuted after cooling, granulated and spun to threads in usual manner or pressed to foils.

The threads of foils thus obtained had a brilliant appearance and a good fastness to light.

EXAMPLE 4

1000 Parts by weight of ε-caprolactame were melted at about 100°C in a glass apparatus continuously maintained under nitrogen provided with a steel stirrer and a descending cooler. Calculated on the amount of caprolactame used, 0.08 % of the compound (101) and 0.34 % of a 12 % aqueous TiO$_2$ suspension were added. The mixture was heated while stirring for one hour to 175°–180°C. After one hour the temperature was further raised to 275°C and the whole was stirred for about 5 hours at this temperature. At the end of the reaction time, a stronger stream of nitrogen was introduced, in order to distill off the lactame in excess. The polyamide melt thus prepared was passed through a slot die to form a ribbon which was quenched in water, chipped and dried.

A fabric obtained from this polycondensate by spinning and knitting showed a much better degree of whiteness of a good fastness to light than a fabric prepared in the same manner, but without addition of a brightener.

EXAMPLE 5

A fabric of polyamide-6 was treated in a wash-liquor having a goods-to-liquor-ratio of 1:20, which contained 6 g/l of a detergent having the following composition:

9.8 % of isotridecanol-polyglycol ether (with, on an average, 8 mols of ethylene oxide units per mol of isotridecanol)

30 % of sodium tripolyphosphate

15 % of tetrasodium pyrophosphate

5 % of sodium metasilicate

2 % of carboxymethyl cellulose (viscosity of a 2 % solution in water at 20°C 1500 cP) and 0.05 % of one of the following compounds (balance to 100 % sodium sulfate).

The fabric was washed at 60°C for 10 minutes, rinsed as usual and dried. This treatment was repeated up to ten times.

After 1 and 10 treatments the polyamide fabrics had the following degrees of whiteness (according to Berger):

|  |  | washed once | washed ten times |
|---|---|---|---|
| compound | (101) | 104 | 131 |
|  | (106) | 111 | 125 |

Untreated good: degree of whiteness 68

EXAMPLE 6

A fabric of polyamide-6 was treated after a usual pre-washing process at a goods-to-liquor ratio of 1:20 on the winch vat with a bath which contained 0.1 g/l of the compound (101) in a dispersed form. The fabric was treated for 30 minutes at 80°C and then rinsed as usual and dried. The fabric showed a very high degree of whiteness of 157 (according to Berger) as compared with 68 for the pre-washed material.

The compound (106) could be used with almost the same effect.

The compounds (101) and (106) may be brought in a dispersed form in the following way:

100 mg of the butadiene compound were dissolved until clear in 5 ml of dimethylformamide by heating, and after addition of 5 ml of an emulsifier on the basis of a nonyl phenol polyglycol ether (with, on an average 23 ethylene-oxide units) poured, while stirring, in a thin jet, into 100 ml of distilled water.

EXAMPLE 7

A fabric of cellulose-2½-acetate was treated on a winch vat at a goods-to-liquor-ratio of 1:20 in a bath which contained 0.1 g/l of the compound (104) in a dispersed form. The fabric was treated for 45 minutes at 85°C, rinsed as usual and dried.

A degree of whiteness according to Berger of 118 was found, whereas the original fibre had a degree of whiteness of 65. The compounds (106) and (101)

could be used with the same good result.

The fine division of the compounds according to the invention was effected as described in Example 6.

EXAMPLE 8

A fabric consisting of at least 85 % of polyacrylonitrile was treated with a bath which contained 0.2 % of the dispersed compound (101) and was adjusted to pH 4 with formic acid. The ratio between material and liquid was calculated in such a way that 1 part of fabric corresponded to 40 parts of the bath. The fabric was introduced at 60°C and heated within 30 minutes to boiling temperature. After a boiling time of 30 minutes the material was rinsed at a decreasing temperature as usual and dried.

The material thus treated had a degree of whiteness according to Berger of 119, the starting material of 69.

The compound (106) could be used with about the same success.

EXAMPLE 9

From a suspension polyvinyl chloride, under addition of 3 % of tritanium dioxide and 0.05 % of the compound (106) a hard foil was prepared by rolling at 80°C for 15 minutes. The foil had a considerably higher degree of whiteness than a foil prepared in the same way but without addition of the brightener.

A similar good effect of the brightener was also observed with foils prepared by using emulsion polyvinyl chloride.

EXAMPLE 10

0.03 Parts of the brightener (106) was added to a plastified foil of polyvinyl chloride which consisted of 75 parts of PVC-powder 25 parts of dioctyl phthalate 2 parts of titanium dioxide (rutile type) and 0.2 part of wax.

The degree of whiteness (according to Berger) of a foil thus brightened was 121.

A foil prepared under the same conditions but without optical brightening had a degree of whiteness according to Berger of 78.8.

Table benzofuranyl-CH=CH—CH=CH—A

| Compound No. | A | Melting point °C | absorption** λmax [m/μ] |
|---|---|---|---|
| 101 | phenyl | 152–154 | 356 |
| 102 | CH$_3$O-phenyl | 170–171* | 362 |
| 103 | NC-phenyl | 182–184* | 381 |
| 104 | biphenylyl | 222–224* | 374 |
| 105 | naphthyl | 151–152 | 380 |
| 106 | naphthyl | 223–225 | 369 |
| 107 | thienyl | 175–176 | 368 |
| 108 | benzofuranyl | 232–235 | 380 |

*forms "liquid crystals"
**in dimethylformamide

We claim:
1. A compound of the formula
   A-CH=CH-CH=CH-B
in which A is phenyl, naphthyl, 2-thienyl, 2-furanyl or 2-benzofuranyl which radicals are unsubstituted or substituted by lower alkyl, lower alkoxy, phenyl, carboxy, sulfo, cyano or lower carboalkoxy; and B is 2-benzofuranyl or lower alkyl-2-benzofuranyl.

2. A compound as defined in claim 1, wherein A is phenyl, naphthyl, 2-thienyl, 2-furanyl, 2-benzofuranyl or phenyl substituted by lower alkyl, lower alkoxy, phenyl, carboxy, sulfo, cyano or lower carboalkoxy.

3. A compound as defined in claim 1, wherein A is phenyl, lower alkoxyphenyl, cyanophenyl, biphenylyl, naphthyl, 2-thienyl or 2-benzofuranyl and B is 2-benzofuranyl.

4. The compound as defined in claim 1, wherein A is phenyl and B is 2-benzofuranyl.

5. The compound as defined in claim 1, wherein A is 1-naphthyl and B is 2-benzofuranyl.

6. The compound as defined in claim 1, wherein A is 2-naphthyl and B is 2-benzofuranyl.

7. The compound as defined in claim 1, wherein A and B are 2-benzofuranyl.

* * * * *